US008977347B2

(12) United States Patent
Mestha et al.

(10) Patent No.: US 8,977,347 B2
(45) Date of Patent: Mar. 10, 2015

(54) VIDEO-BASED ESTIMATION OF HEART RATE VARIABILITY

(75) Inventors: Lalit Keshav Mestha, Fairport, NY (US); Survi Kyal, Rochester, NY (US); Beilei Xu, Penfield, NY (US); Himanshu J. Madhu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 10 days.

(21) Appl. No.: 13/532,057

(22) Filed: Jun. 25, 2012

(65) Prior Publication Data

US 2013/0345568 A1 Dec. 26, 2013

(51) Int. Cl.
*A61B 5/024* (2006.01)

(52) U.S. Cl.
USPC .............................. 600/473; 600/479; 702/19

(58) Field of Classification Search
None
See application file for complete search history.

(56) References Cited

U.S. PATENT DOCUMENTS

| | | | | |
|---|---|---|---|---|
| 5,860,917 | A * | 1/1999 | Comanor et al. | 600/300 |
| 7,336,982 | B2 | 2/2008 | Yoo | |
| 7,885,477 | B2 * | 2/2011 | Ito et al. | 382/254 |
| 8,526,765 | B2 * | 9/2013 | Sakaguchi et al. | 382/299 |
| 8,538,200 | B2 * | 9/2013 | Wang et al. | 382/299 |
| 8,588,545 | B2 * | 11/2013 | Wedi et al. | 382/275 |
| 8,792,969 | B2 * | 7/2014 | Bernal et al. | 600/476 |
| 8,838,209 | B2 * | 9/2014 | Mestha et al. | 600/473 |
| 2006/0293921 | A1 * | 12/2006 | McCarthy et al. | 705/2 |
| 2008/0004539 | A1 * | 1/2008 | Ross | 600/509 |
| 2010/0274144 | A1 * | 10/2010 | Hu et al. | 600/500 |
| 2011/0060235 | A1 * | 3/2011 | Crompvoets et al. | 600/509 |
| 2011/0251493 | A1 | 10/2011 | Poh et al. | |
| 2012/0190947 | A1 * | 7/2012 | Chon et al. | 600/323 |
| 2013/0274610 | A1 * | 10/2013 | Kamshilin et al. | 600/473 |
| 2013/0296660 | A1 * | 11/2013 | Tsien et al. | 600/301 |
| 2013/0331669 | A1 * | 12/2013 | Berte et al. | 600/324 |
| 2014/0243621 | A1 * | 8/2014 | Weng et al. | 600/301 |
| 2014/0303454 | A1 * | 10/2014 | Clifton et al. | 600/301 |

OTHER PUBLICATIONS

M.P. Tarvainen et al., "An Advanced De-Trending Method With Application to HRV Analysis", IEEE Trans. Biomed. Eng., vol. 49, No. 2, pp. 172-175 (2002).*
Wei Lu et al., "Approach and Applications of Constrained ICA", IEEE Transactions on Neural Networks, vol. 16, No. 1, Jan. 2005.

(Continued)

*Primary Examiner* — Long V Le
*Assistant Examiner* — Kevin Pontius
(74) *Attorney, Agent, or Firm* — Philip E. Blair; Fleit Gibbons Gutman Bongini & Bianco P.L.

(57) ABSTRACT

What is disclosed is a video-based system and method for estimating heart rate variability from time-series signals generated from video images captured of a subject of interest being monitored for cardiac function. In a manner more fully disclosed herein, low frequency and high frequency components are extracted from a time-series signal obtained by processing a video of the subject being monitored. A ratio of the low and high frequency of the integrated power spectrum within these components is computed. Analysis of the dynamics of this ratio over time is used to estimate heart rate variability. The teachings hereof can be used in a continuous monitoring mode with a relatively high degree of measurement accuracy and find their uses in a variety of diverse applications such as, for instance, emergency rooms, cardiac intensive care units, neonatal intensive care units, and various telemedicine applications.

20 Claims, 7 Drawing Sheets

(56) References Cited

OTHER PUBLICATIONS

Wei Lu et al., "Constrained Independent Component Analysis", School of Computer Engineering, Nanyang Technological University, Singapore 639798.

Takano et al., "Heart rate measurement based on a time-lapse image", Medical Engineering & Physics 29 (2007), pp. 853-857, www.sciencedirect.com.

Poh et al., "Non-contact, automated cardiac pulse measurements using video imaging and blind source separation.", May 10, 2010, vol. 18, No. 10 / Optics Express 10762.

Lee et al., "Temporally constrained ICA-based foetal ECG separation", Electronics Letters, Oct. 13, 2005, vol. 41, No. 21.

Mestha et al., "Systems and Methods for Non-Contact Heart Rate Sensing", U.S. Appl. No. 13/247,575, filed Sep. 28, 2011.

Xu et al., "A Multi-Layer Array for a Multi-Resolution Multi-Spectral Camera," U.S. Appl. No. 13/239,642, filed Sep. 22, 2011.

Yang et al., "Vital Sign Estimation from Passive Thermal Video," IEEE Conference on Computer Vision and Pattern Recognition, Jun. 2008, pp. 23-28.

Garbey et al., "Contact-Free Measurement of Cardiac Pulse Based on the Analysis of Thermal Imagery," IEEE Transactions on Biomedical Engineering, Aug. 2007, vol. 54, No. 8, pp. 2-13.

Mestha et al., "Method for Classifying a Pixel of a Hyperspectral Image in a Remote Sensing Application," U.S. Appl. No. 13/023,310, filed Feb. 8, 2011.

Wang et al., "Determining a Total Number of People in a IR Image Obtained Via an IR Imaging System," U.S. Appl. No. 12/967,775, filed Dec. 14, 2010.

Xu et al., "System and Method for Object Identification and Tracking," U.S. Appl. No. 13/247,343, filed Sep. 28, 2011.

Lee et al., "Speech Coding and Noise Reduction Using Ice-Based Speech Features," in P. Pajunen and J. Karhunen (eds.), Proc. Second International Workshop on Independent Component and Analysis and Blind Signal Separation, 2000.

Hoyer et al., "ICA Features of Colour and Stereo Images," P. Pajunen and J. Karhunen (eds.), Proc. Second International Workshop on Independent Component and Analysis and Blind Signal Separation, 2000, pp. 567-572.

Bell et al., "The "Independent Components" of Natural Science are Edge Filters," Vision Ref., 1997, vol. 37, No. 23, pp. 3327-3338.

Lee et al., "Application of independent component analysis to microarrays," Genome Biology, 2003, vol. 4, Issue 11, R76.

Cantelli, Mark, "Are you in There?" Tolltrans 2011, www.TrafficTechnologyToday.com.

Mestha, et al., "Estimating Cardiac Pulse Recovery From Multi-Channel Source Data Via Constrained Source Separation", U.S. Appl. No. 13/247,683, filed Sep. 28, 2011.

Mestha et al., "Filtering Source Video Data Via Independent Component Selection", U.S. Appl. No. 13/281,975, filed Nov. 8, 2011.

Cardoso, Jean-Francois, "Blind signal separation: statistical principles", pp. 1-16, (Official Version published as: Proceedings of the IEEE, vol. 9, No. 10, pp. 2009-2025, Oct. 1998).

Hyvarinen et al., "Independent Component Analysis: Algorithms and Applications", Neural Networks Research Centre, Helsinki University of Technology, Finland, Neutral Networks, pp. 1-31, 13(4-5); 411-430, 2000.

Wang et al., "Determining a Number of Objects in an IR Image", U.S. Appl. No. 13/086,006, filed Apr. 28, 2011.

Wang, et al., "Post-Processing a Multi-Spectral Image for Enhanced Object Identification", U.S. Appl. No. 13/324,368, filed Dec. 28, 2011.

Mestha et al., "Removing Environment Factors From Video Signals Captured for Biomedical Measurements", U.S. Appl. No. 13/401,207, filed Feb. 21, 2012.

Pressman et al., "A Transducer for the Continuous External Measurement of Arterial Blood Pressure", External Measurement of Blood Pressure, IEEE Transactions on Bio-Medical Electronics, Apr. 1963, pp. 73-81.

Meigas et al., "Continuous Blood Pressure Monitoring Using Pulse Wave Delay", Proposed Paper; Engineering in Medicine and Biology Society, 2001, vol. 4, pp. 3171-3174, Proceedings of the 23rd Annual Int'l Conf. of the IEEE.

Penaz, J., "Photoelectric Measurement of Blood Pressure, Volume and Flow in the Finger", Dresden, 10th Int. Conf. Med. and Biol. Engineering, 1973, Session 7, N2, Haemodynamics I, pp. 161-164.

Aubert et al., "A Model-Based Study of the Influence of Vaso-Active Drugs on Pulse Delays Measured from the Electrocardiogram", Computers in Cardiology 2007:34:383-386.

Naschitz et al., "Pulse Transit Time by R-Wave-Gated Infrared Photoplethysmography: Review of the Literature and Personal Experience", Journal of Clinical Monitoring and Computing (2004) 18: 333-342, Springer 2005.

Reisner et al., "Utility of the Photoplethysmogram in Circulatory Monitoring", Anesthesiology, vol. 108, No. 5, May 2008, pp. 950-958.

Dalal et al., "Histograms of Oriented Gradients for Human Detection", Proceedings of the Conference on Computer Vision and Pattern Recognition, San Diego, California, USA, pp. 886-893, (2005).

Skaff et al., "Estimating a Visible Vector Representation for Pixels in an Infrared Image", U.S. Appl. No. 13/364,835, filed Feb. 2, 2012.

Xu et al., "Subcutaneous Vein Pattern Detection Via Multi-Spectral IR Imaging in an Identity Verification System", U.S. Appl. No. 13/087,850, filed Apr. 15, 2011.

Mestha et al., "Deriving Arterial Pulse Transit Time From a Source Video Image", U.S. Appl. No. 13/401,286, filed Feb. 21, 2012.

Piratla et al., "Web-Based System and Method for Video Analysis", U.S. Appl. No. 13/417,979, filed Mar. 12, 2012.

Xu et al., "Monitoring Respiration With a Thermal Imaging System", U.S. Appl. No. 13/103,406, filed May 9, 2011.

Wang et al., "Multi-Band Infrared Camera System Optimized for Skin Detection", U.S. Appl. No. 13/416,436, filed Mar. 9, 2012.

Mestha et al., "Processing a Video for Vascular Pattern Detection and Cardiac Function Analysis", U.S. Appl. No. 13/483,992, filed May 30, 2012.

Mestha et al., "A Multi-Filter Array for a Multi-Resolution Multi-Spectral Camera", U.S. Appl. No. 13/239,642, filed Sep. 22, 2011.

Tarvainen et al., "An Advanced De-Trending Method With Application to HRV Analysis", IEEE Trans. Biomed. Eng., vol. 49, No. 2, pp. 172-175, Feb. 2002.

Sahoo et al., "Detection of Atrial Fibrillation from Non-Episodic ECG Data: A Review of Methods", 33rd Annual International Conference of the IEEE EMBS, Boston, Massachusetts USA, (Aug. 30-Sep. 3, 2011).

Kikillus et al., "Three Different Algorithms for Identifying Patients Suffering From Atrial Fibrillation During Atrial Fibrillation Free Phases of the ECG", Computers in Cardiology, 34:801-804, (2007).

\* cited by examiner

| NAME | FREQUENCY (Hz) | ASSOCIATIONS WITH |
|---|---|---|
| HR (HEART RATE) | 0.7-4 | CARDIAC PULSE |
| HF (HIGH FREQUENCY) | 0.15-0.4 | PARASYMPATHETIC |
| LF (LOW FREQUENCY) | 0.04-0.15 | SYMPATHETIC AND PARASYMPATHETIC |
| VLF (VERY LOW FREQUENCY) | 0.003-0.04 | NOT WELL DEFINED |
| ULF (ULTRA LOW FREQUENCY) | <0.003 | DAY AND NIGHT DIFFERENCES |
| RR (RESPIRATION RATE) | 0.2-0.7 (UPPER LIMIT: >1.6 IN SICK INFANTS) | PULMONARY VENTILATION |

VIDEO-BASED ESTIMATION OF HEART RATE VARIABILITY

TECHNICAL FIELD

The present invention is directed to systems and methods for estimating heart rate variability from video captured of a patient being monitored for cardiac function.

BACKGROUND

The Autonomic Nervous System (ANS) is represented by the sympathetic and parasympathetic nervous systems (SNS and PSNS). These function in opposition to each other. The sympathetic system typically functions to initiate immediate actions that require a quick physical response such as to quickly pull a hand away from a hot flame. In contrast, the parasympathetic system is associated with actions that do not require immediate reaction. Heart rate variability (HRV) is an established quantitative marker to obtain a quick superficial reflection of the state of the ANS. Heart rate variability is the beat-to-beat time variation in heart beat and is modulated primarily by the ANS via changes in the balance between parasympathetic and sympathetic influences. Heart rate is automatically adjusted in response to stress, respiration, metabolic changes, thermo-regulation, physical exertion, endocrine cycles, and the like. HRV is also useful for the diagnosis of various diseases and health conditions such as diabetic neuropathy, cardiovascular disease, myocardial infarction, fatigue, sleep problems, and others.

Systems have arisen in this art to estimate HRV. For example, HRV can be estimated by monitoring the electrical activity of the heart using, for example, a contact-based electro-cardiogram device (ECG) where HRV signals are generated by extracting the intervals between R-waves from the ECG. Due to the complex morphology of the ECG signals, locating the R-waves and its peaks to find the time intervals between peaks (RR interval) can result in an erroneous HRV result. Ectopic beats, arrhythmic events, missing data, environmental noise, and the like, may also contribute to inaccurate HRV measurements. When compared to contact-based ECG methods, non-contact methods provide the practitioner with the additional flexibility of being able to access different regions of the body where it may be hard to get signals using wires and probes. Moreover, signals obtained via non-contact methods can be improved by integrating over a larger region of interest when compared to contact-based ECG systems since ECG only provides signals that are localized to relatively small regions where the sensors were attached. Unobtrusive, non-contact methods to obtain HRV measures from a resting cardiac patient are desirable in this art.

Accordingly, what is needed in this art is a video-based system and method for estimating heart rate variability from time-series signals generated from video images captured of a subject of interest being monitored for cardiac function.

INCORPORATED REFERENCES

The following U.S. patents, U.S. patent applications, and Publications are incorporated herein in their entirety by reference.

"Processing A Video For Vascular Pattern Detection And Cardiac Function Analysis", U.S. patent application Ser. No. 13/483,992, by Mestha et al.

"Estimating Cardiac Pulse Recovery From Multi-Channel Source Data Via Constrained Source Separation", U.S. patent application Ser. No. 13/247,683, by Mestha et al.

"Multi-Band Infrared Camera System Optimized For Skin Detection", U.S. patent application Ser. No. 13/416,436, by Wang et al.

"A Multi-Filter Array For A Multi-Resolution Multi-Spectral Camera", U.S. patent application Ser. No. 13/239,642, by Xu et al.

"Subcutaneous Vein Pattern Detection Via Multi-Spectral IR Imaging In An Identity Verification System", U.S. patent application Ser. No. 13/087,850, by Xu et al.

"Deriving Arterial Pulse Transit Time From A Source Video Image", U.S. patent application Ser. No. 13/401,286, by Mestha.

"Filtering Source Video Data Via Independent Component Selection", U.S. patent application Ser. No. 13/289,975, by Mestha et al.

"Removing Environment Factors From Signals Generated From Video Images Captured For Biomedical Measurements", U.S. patent application Ser. No. 13/401,207, by Mestha et al.

"*Blind Signal Separation: Statistical Principles*", Jean-Francois Cardoso, Proceedings of the IEEE, Vol. 9, No. 10, pp. 2009-2025, (October 1998).

"*Independent Component Analysis: Algorithms And Applications*", Aapo Hyvärinen and Erkki Oja, Neural Networks, 13(4-5), pp. 411-430, (2000).

"*An Advanced De-Trending Method With Application To HRV Analysis*", M. P. Tarvainen, P. O. Ranta-Aho, and P. A. Karjalainen, IEEE Trans. Biomed. Eng., vol. 49, no. 2, pp. 172-175, February 2002.

BRIEF SUMMARY

What is disclosed is a video-based system and method for estimating heart rate variability from time-series signals generated from video images captured of a subject of interest being monitored for cardiac function. In a manner more fully disclosed herein, low frequency and high frequency components are extracted from a time-series signal obtained by processing a video of the subject being monitored. A ratio of the low and high frequency of the integrated power spectrum within these components is computed. Analysis of this ratio over time provides the estimated heart rate variability. The teachings hereof can be used in a continuous monitoring mode with a relatively high degree of measurement accuracy and, advantageously, find their intended uses in a variety of settings such as, for instance, emergency rooms, cardiac intensive care units, neonatal intensive care units, including various telemedicine applications.

One embodiment of the present video-based system and method for estimating heart rate variability involves the following. First, a video is received which captures a target area of a region of exposed skin of a subject of interest where photoplethysmograph (PPG) signals can be registered. The video comprises a plurality of time-varying video images captured by a video camera with at least one imaging channel. The video images are processed such that a time-series signal corresponding to PPG signals captured by the imaging channel are isolated. Then, for a pre-defined time interval, low frequency and high frequency components of the integrated power spectrum within the time-series signal are extracted. In advance of extracting the low and high frequency components, the PPG signal may be de-trended to remove slow non-stationary trends from the signal such that a nearly stationary PPG signal can be obtained. Thereafter, a ratio of the low and high frequency is determined over the time interval. The ratio comprises the subject's estimated heart rate variability for that time interval. The estimated heart rate variability is then communicated to a display device or a storage device.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which:

FIG. 4 shows the HRV assessment using the methods disclosed herein, with (4A) showing the power spectrum exhibiting dominant LF, i.e., both sympathetic and parasympathetic influence, and (4B) showing the power spectrum exhibiting dominant HF, i.e., parasympathetic influence;

DETAILED DESCRIPTION

What is disclosed is a video-based system and method for estimating heart rate variability from time-series signals generated from video images captured of a subject of interest being monitored for cardiac function in a unobtrusive, non-contact, remote sensing environment.

NON-LIMITING DEFINITIONS

A "video" is a time-varying sequence of images captured of a subject of interest using a video camera capable of acquiring a video signal over at least one data acquisition (imaging) channels. The video may also contain other components such as, audio, time reference signals, noise, and the like.

A "subject of interest" refers to a human having a cardiac function for which heart rate variability measurements are intended to be determined in accordance with the teachings hereof. Although the term "human", "person", or "patient" may be used throughout this text, it should be appreciated that the subject of interest may be something other than a human being such as, for instance, an animal. Use of "person" or "patient" is not to be viewed as limiting the appended claims strictly to humans.

A "region of exposed skin" is an unobstructed area of the subject's skin where a PPG signal of the subject can be registered. Such regions can be identified in image frames of a video using, for example, object identification, pixel classification, material analysis, texture identification, and pattern recognition methods.

A "time-series signal" refers to a time varying signal generated from images of the captured video. Time-series signals may be generated in real-time from a streaming video as in the case of continuous patient monitoring. The time-series signal may be obtained directly from the data acquisition channel of the video camera used to capture the video of the subject of interest. The time-series signal may be retrieved from a remote device such as a computer workstation over a wired or wireless network or obtained on a continuous basis from a video stream.

A "video camera" is a device for acquiring a video. In one embodiment, the video camera comprises a color video camera with at least one imaging channel for capturing color values for pixels corresponding generally to the primary visible colors (typically RGB). In another embodiment, the video camera is an infrared camera with at least one imaging channel for measuring pixel intensity values in the NIR wavelength range. In another embodiment, the video camera is a hybrid device capable of capturing both color and NIR video images.

A "video analysis module", in one embodiment, is a hardware device with at least one processor executing machine readable program instructions for analyzing video images such that the subject's heart rate variability can be determined. Such a module may comprise, in whole or in part, a software application working alone or in conjunction with one or more hardware resources. Such software applications may be executed by processors on different hardware platforms or emulated in a virtual environment. Aspects of the video analysis module may leverage off-the-shelf software.

"Cardiac function" refers to the function of the heart and, to a large extent, to the cardio-vascular system. In most species, the heart comprises a muscle which repeatedly contracts to pump blood through vascular network. Cardiac function can be impacted by a variety of factors including age, stress, disease, overall health, and the like. Cardiac function can also be affected by environmental conditions such as altitude and pressure.

"Cardiac pulse" is a pressure wave that is generated by the subject's heart (in systole) as the heart pushes a volume of blood into the arterial pathway. Arterial movement, as a result of this pressure wave, can be sensed by tactile and electronic methods. A frequency range of the cardiac pulse is the pulse rate measured over time, typically recorded in beats per minute (bpm). The frequency range of the human cardiac pulse is between about 50 bpm to 240 bmp. A resting adult human has a heart rate of about 72 bpm. Each species has their own cardiac pulse frequency range and thus their own "normal" heart rate. Heart rate is proportional to cardiac output, i.e., the volume of blood the heart can pump expressed in L/min (~5 L/min in an adult human). Methods used to detect beats include: ECG, blood pressure, and the pulse wave signal derived from a photoplethysmographic (PPG) signal. ECG is widely used because it provides a clear waveform which makes it easier to exclude heartbeats not originating in the sinoatrial node.

Figure 1:
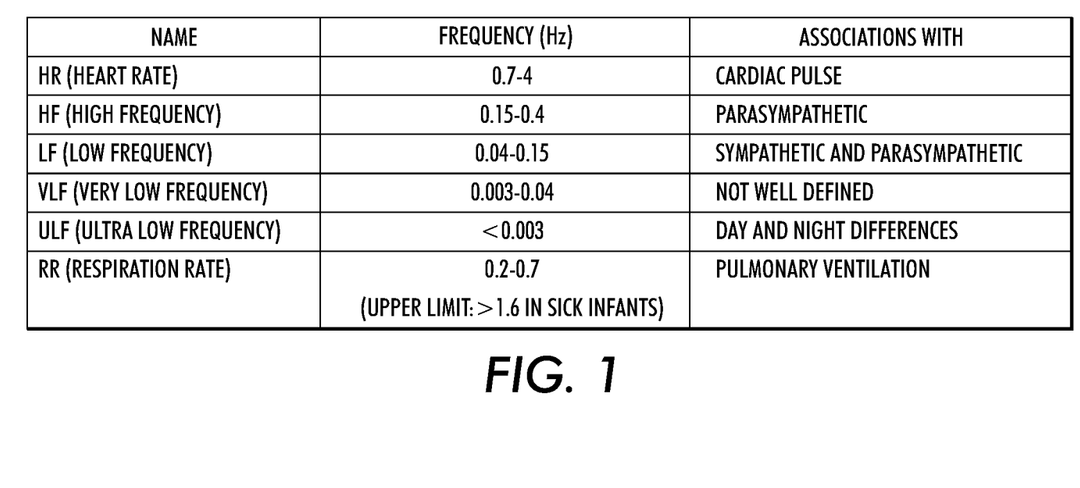
FIG. 1 is a Table which summarizes the spectral components of various HR signals for explanatory purposes.

"Heart Rate Variability" (HRV) is where the time interval between heart beats varies. Variation in the beat-to-beat interval is a physiological phenomenon. The SA node receives several different inputs and the instantaneous heart rate or RR interval and its variation are the results of these inputs. The main inputs are the sympathetic nervous system (SNS) and the parasympathetic nervous system (PSNS) and humoral factors. Respiration gives rise to waves in heart rate mediated primarily via the PSNS. Factors that affect the input include the baroreflex, thermoregulation, hormones, sleep-wake cycle, meals, physical activity, and stress. Decreased PSNS activity or increased SNS activity will result in reduced HRV. HRV is also known by other terms including: Heart Period Variability, Cycle Length Variability, and RR Variability where R is a point corresponding to the peak of the QRS complex of the ECG wave and RR is the interval between successive Rs. Spectral analysis of R-waves, i.e., RR interval of a 2 to 5 minute short ECG recording, contains the following components: (1) a very low frequency (VLF) component at a frequency range that is ≤0.04 Hz; (2) a low frequency (LF) component that is within 0.04 to 0.15 Hz; and (3) a high frequency (HF) component that is within 0.15 to 0.40 Hz. There is also an ultra-low frequency component (ULF) which is associated with day and night differences at frequencies <0.003 Hz which are typically observed when the signals have been captured over a period of 18 hours or longer. The physiological explanation of the VLF component is less defined and hence it is not considered in a HRV analysis. The TABLE of FIG. 1 summarizes the spectral components of HR signals.

A "photoplethysmographic signal", or simply PPG signal, is a signal which correlates to the subject's cardiac pulse pressure wave. In one embodiment, a region of exposed skin of the subject where such pressure waves can be registered such as, for example, a neck or chest area, is captured by a video camera. The video images are processed to isolate a vascular pattern. One method for identifying subcutaneous vascular patterns is disclosed in the above-incorporated US patent application entitled: "Subcutaneous Vein Pattern Detection Via Multi-Spectral IR Imaging In An Identity Verification System", by Xu et al, which teaches that blood vessels in the isolated vascular pattern are identified across image frames and processed to obtain a time-series signal. The vascular network/pattern is identified in the video images based on, for example, color, spatial features, material identification, and the like. An average of all pixel values in the identified vascular regions within each image frame of the captured video is computed to obtain a channel average on a per-frame basis. A global channel average is computed, for each channel, by adding the channel averages across multiple image frames and dividing by the total number of frames. The channel average is subtracted from the global channel average and the result divided by a global channel standard deviation to obtain a zero-mean unit variance time-series signal for each of the isolated vascular regions. The obtained time-series signal are normalized and filtered to remove undesirable frequencies. The resulting time-series signals for the vascular regions contain the sum total of volumetric pressure changes within those regions. Arterial pulsations comprise a dominant component of these signals. The signals are processed using an independent component analysis technique to extract PPG signals. The above-incorporated US patent application entitled: "Processing A Video For Vascular Pattern Detection And Cardiac Function Analysis", by Mestha et al., describes a method to isolate veins and arterial networks/patterns in NIR video images.

For vascular pathway detection, the video may be pre-processed to compensate for non-uniform illumination due to a curvature of a surface of the region of exposed skin. The video may be processed to compensate for motion induced blur, imaging blur, or slow illuminant variation. Smoothing may be performed on the video to remove skin texture from a surface of the region of exposed skin. Smoothing can be effectuated using, for example, a Gaussian smoothing as is well understood. The video may be processed to enhance contrast or brightness. Independent component selection can also be used to emphasize certain content in the video such as, for example, a region containing larger blood vessels. If camera-related noise or environmental factors are adversely affecting extraction of cardiac signals, compensation can be effectuated using the teachings described in the above-incorporated US patent application entitled: "Removing Environment Factors From Signals Generated From Video Images Captured For Biomedical Measurements", by Mestha et al. Post-compensated video signals contain decorrelated and noise corrected channels on a per-frame basis.

A "remote sensing environment" refers to a non-invasive means of acquiring a PPG signal from a subject of interest. The sensing device can be any distance away from the subject. The teachings hereof find their intended uses in an environment such that the resting cardiac patient remains undisturbed and is free of bodily attachments.

Example Image Capture System

Figure 2:
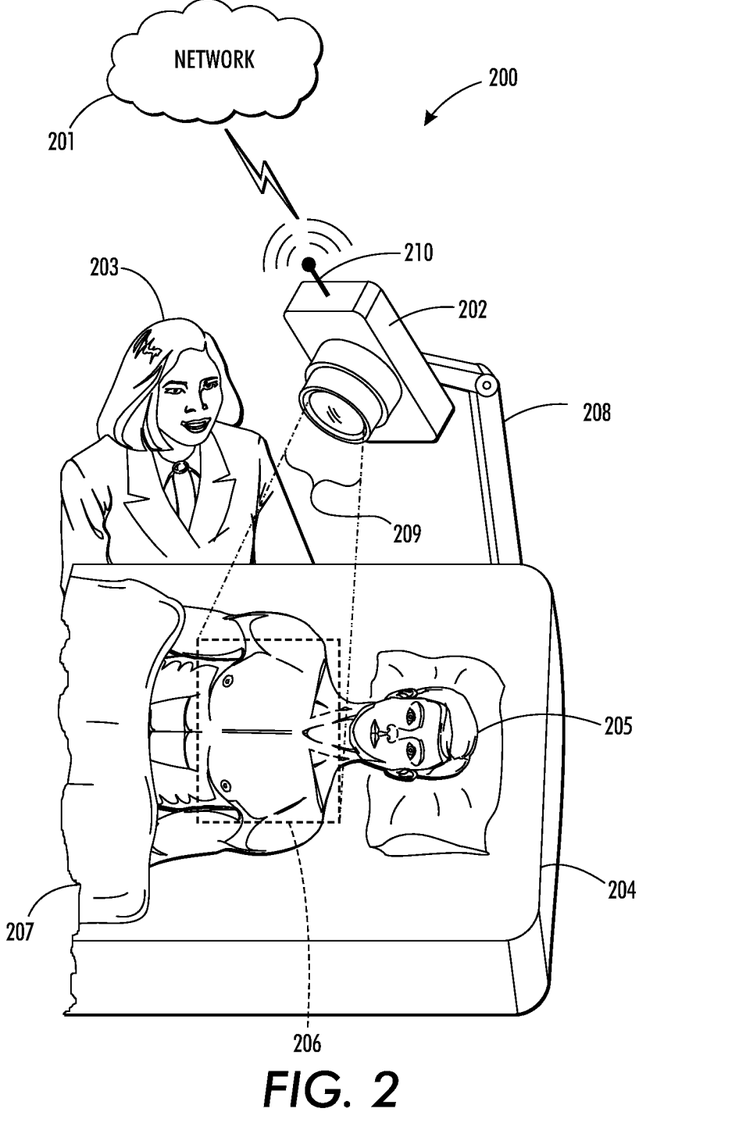
FIG. 2 illustrates an example imaging system for capturing a video signal of a subject of interest.

Reference is now being made to FIG. 2 which illustrates an example imaging system for capturing a video signal of a subject of interest. Examination room 200 has an example image capturing system 202 being operated by technician 203 standing at the bedside 204 of subject of interest 205 shown resting his head on a pillow while his body is partially covered by sheet 207. Camera system 202 is rotatably fixed to support arm 208 such that the camera's field of view 209 can be directed by nurse 203 onto an area of exposed skin of a chest area 206 of patient 205 for continuous monitoring of cardiac function. Support arm 208 is on a set of wheels so that the image capture system can be moved from bed to bed and room to room. Although patient 205 is shown in a prone position lying in a bed, it should be appreciated that images of the subject of interest being monitored for cardiac function can be captured while the subject is positioned in other supporting devices such as, for example, a chair or wheelchair, standing up, including walking or moving.

Camera system 202 captures video images of the subject of interest to be monitored for cardiac function. The captured video images comprises multi-channel source data such as RGB and/or multi-spectral acquired over time. Camera 202 comprises imaging sensors which may be a single sensor or a sensor array including a plurality of individual or separate sensor units. A central processor integral to camera 202 and in communication with a memory (not shown) functions to detect changes in the status of sensors and outputting an alarm, notice, report, and the like, if a change in any hardware or software of the camera has been detected. Other sensors are capable of sensing a change of status of patient 205 and issue an alarm or notification via transmission element 210 to a nurse, doctor, or technician in the event that the monitored cardiac function of the patient falls outside a set of pre-defined parameters.

Antenna 210 is used to communicate the video images to various remote devices. Transmitter 210 may be a wired (e.g., Ethernet) connection utilizing an Ethernet network consisting of Ethernet cables and an Ethernet hub that is in communication with a network 201. Camera system 202 may include both wireless and wired elements and may be connected via other means such as coaxial cable, radio frequency, Bluetooth, or any other manner for communicating data. Network 201 receives the transmitted video signals and wirelessly communicates the received video images to various devices such as, for instance, a workstation with a display device, for processing. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway. Techniques for placing devices in networked communication are well established. A further discussion as to specific techniques for networking devices has been omitted. Any of the networked devices may include a network interface card or system.

Flow Diagram of Example Embodiment

Figure 3:
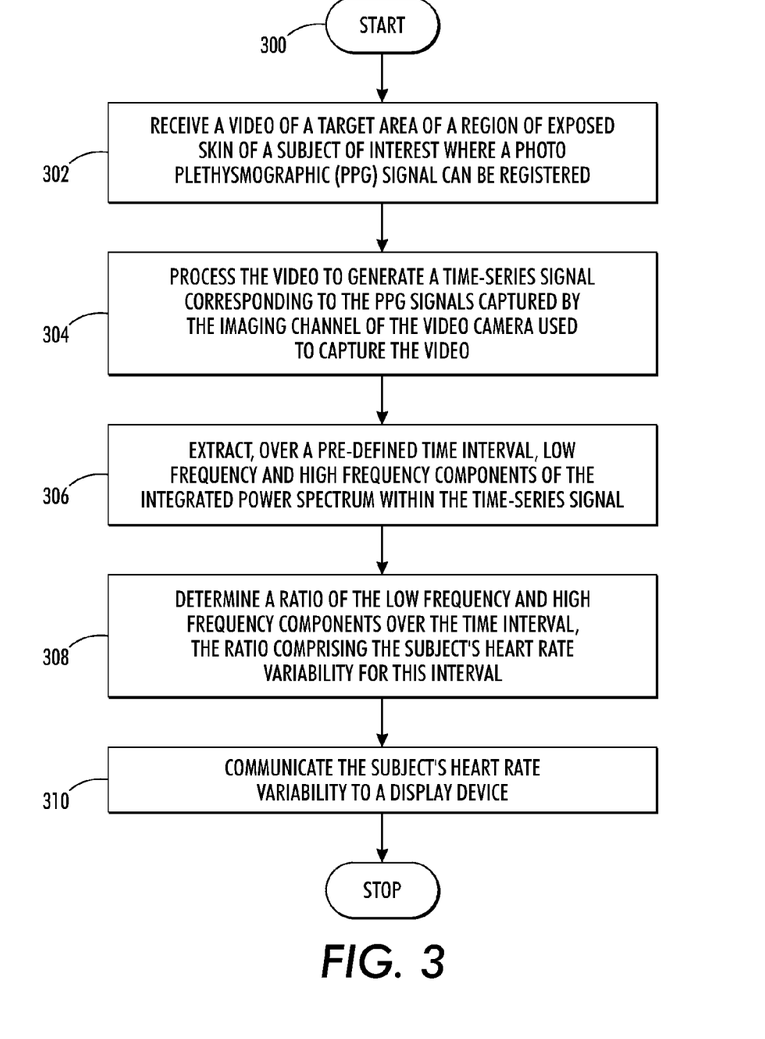
FIG. 3 illustrates one example embodiment of the present method for estimating heart rate variability from a video captured of a subject of interest.

Reference is now being made to the flow diagram of FIG. 3 which illustrates one example embodiment of the present method for estimating heart rate variability from a video captured of a subject of interest. Flow processing begins at step 300 and immediately proceeds to step 302.

At step 302, receive a video of a target area of a region of exposed skin of a subject of interest where a photoplethysmographic (PPG) signal of the subject can be registered. The video comprises a plurality of time-varying images captured by a video camera with at least one imaging channel.

At step 304, process the video images to generate a time-series signal corresponding to PPG signals captured by the imaging channel of the video camera used to capture the video.

At step 306, extract, over a pre-defined time interval, low frequency and high frequency components of the integrated power spectrum within the time-series signal.

At step 308, determine a ratio of the low and high frequency components over the time interval, the ratio comprising the estimated heart rate variability for this interval.

At step 310, communicate the heart rate variability to a display device. One such display device is shown and discussed with respect to the workstation of FIG. 7. In this particular embodiment, further processing stops. In other embodiment, an alarm is initiated which indicates that the subject's heart rate variability is not within acceptable parameters. Initiating an alarm can be, for example, activating a light, making an audible noise, or otherwise generating a signal which activates a device which, in turn, performs an action or provides a notification. The kind of alarm signal being generated will depend on the particular embodiment wherein the teachings hereof are implemented. In this particular alternative embodiment, once the alarm signal is activated, further processing stops. In another embodiment, processing repeats such that the subject's cardiac function is continuously monitored. The present system can be used in conjunction with other health monitoring equipment or integrated therewith such that the initiated alarm signal causes these other device to perform intended functions.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

De-Trending the Time-Series Signal

A slow varying trend in the time-series signal can lead to a non-stationary signal component, which can lead to large sub-bands around the key HRV frequency components. Hence, before performing spectral analysis, it is preferable to de-trend the signal to remove slow non-stationary trends from the signal before HRV analysis. One method for de-trending is described in the above-incorporated reference: "An Advanced De-Trending Method With Application To HRV Analysis". It operates like a time-varying high pass FIR filter by removing low frequency components. In one embodiment, the stationary PPG signal is given by:

$$P_{stat} = (I - (I + \lambda^2 D_2^T D_2)^{-1}) * P_{original} \quad (1)$$

where, I is an identity matrix, $P_{original}$ is a normalized zero-removed time-series signal, $\lambda$ is a user-defined single parameter used to adjust a frequency response of said de-trending algorithm, and $D_2$ is a second order difference matrix of the form:

$$D_2 = \begin{bmatrix} 1 & -2 & 1 & 0 & \ldots & 0 \\ 0 & 1 & -2 & 1 & \ddots & \vdots \\ \vdots & \ddots & \ddots & \ddots & \ddots & 0 \\ 0 & \ldots & 0 & 1 & -2 & 1 \end{bmatrix}. \quad (2)$$

If $P_{original}$ is of size N then the identify matrix is of size N×N. For the subjects we tested, we chose $\lambda$=2000. The parameter sets a priori by experimenting on a patient in their clinical/home/work environment with sample data in such a way that it does not lose any useful information from the lower frequency components.

Band Pass Filtering

Subsequent to de-trending, stationary time series signal, $P_{stat}$, is pre-filtered by a band pass filter to limit the range to retain frequency bands of interest. The time series signal contains frequency components related to heart rate as well as frequencies related to HRV. Pre-filtering removes undesirable frequencies below and above the expected frequency range. Also, the ambient illuminator may be fluctuating at higher beat frequency. For the subjects we tested with a commercial RGB camera, a very wide spectral range was used, i.e., of 0.04 Hz to 2 Hz. A higher order band limited Finite Impulse Response (FIR) filter was used to constrain the band width.

Power Spectral Density and Peak Detection

Power spectral density analysis provides the basic information on how power is distributed as a function of frequency. A power spectral density graph can be obtained using MATLAB "periodogram" function with a hamming window for the filtered stationary signal. Non-parametric approaches such as the autoregressive (AR) time-series modeling can also be used in place of the periodogram approach.

Performance Results

Figure 4A:
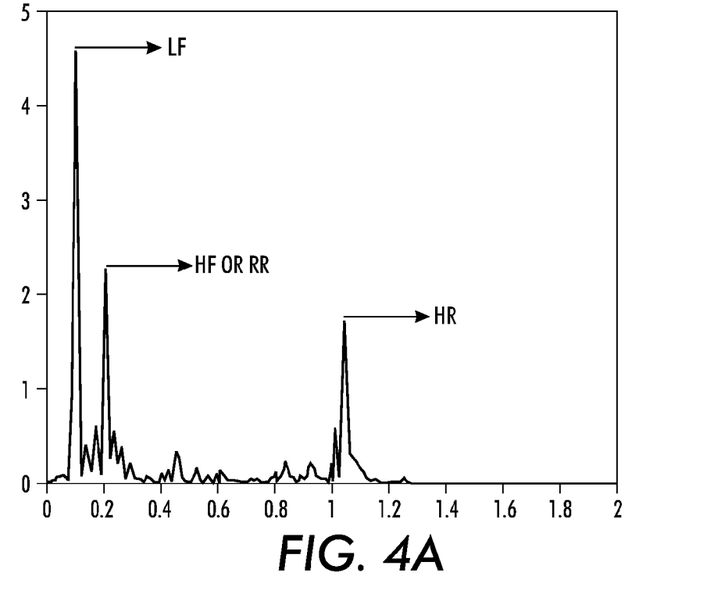
Figure 4B:
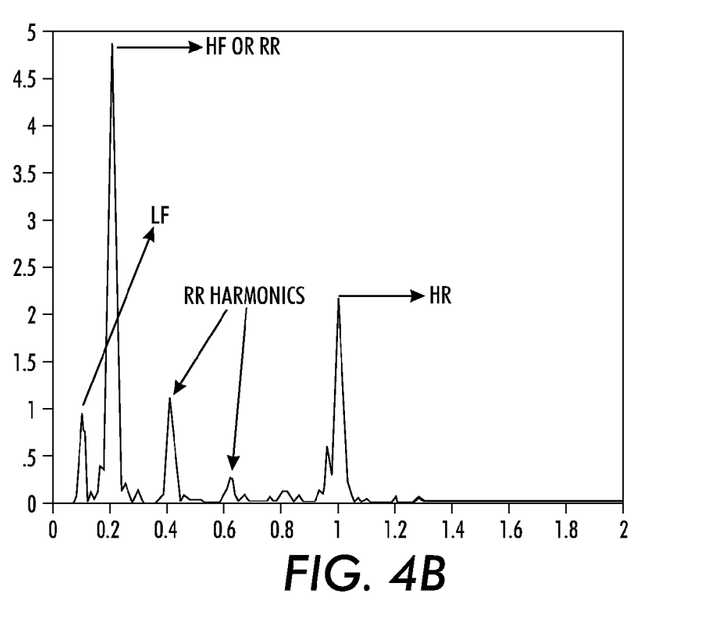
Figure 5A:
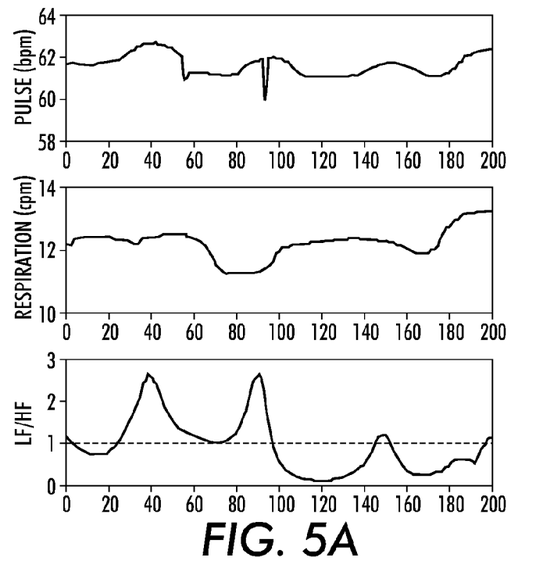
FIG. 5 shows continuous monitoring of HR, RR and HRV or LF/HF for both (5A) sympathetic and (5B) parasympathetic cases for the same subject over a three minute time interval.
Figure 5B:
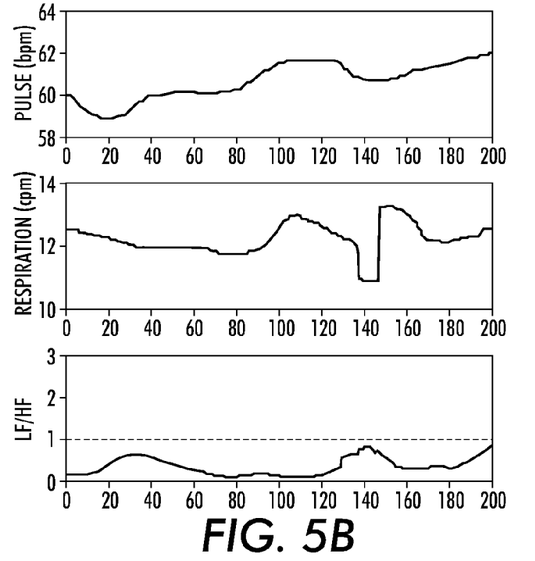

For HRV and sympathetic/parasympathetic analysis, we ran tests for both an adult and an infant. For the adult, we used two videos which are captured in a laboratory setting—one when the participant (of age 24 years old) was sitting still in front of a RGB camera doing usual activity (for sympathetic analysis), and the other when the same participant was passively viewing a video playing a recording (for parasympathetic analysis). For the infant, we used a video recorded in a neonatal intensive care unit (NICU) where the baby/participant was sleeping throughout the recording, only slight movements were observable for a few seconds. All video recordings were produced using a standard RGB digital camera at 30 frames per second (fps) with pixel resolution of 640×480 and saved in AVI format. Each video was three minutes or longer for better understanding of HRV over time. Participant's facial region was selected as the region of exposed skin (ROI). The frames were reduced to time series (RGB channels) by spatially averaging all pixels in the ROI, on a per-frame basis. The green channel trace was chosen as it contained the strongest physiological signals among all channels and de-trended using a smoothing parameter ($\lambda$=2000) for a very low cut-off frequency value of approximately 0.04 Hz for the time-varying FIR high pass filter. The de-trended signal was further processed using a band pass filter with a cut-off frequency of 0.04-2 Hz. Fast Fourier Transform of the processed signal was computed. FIG. 4 shows HRV assessment using this technique. FIG. 4A shows the power spectral density for a sympathetic response and FIG. 4B the same for a parasympathetic response. The LF and HF components were identified using a peak detection algorithm, as are well established in this art. For determining signal strength within each of these components, power spectra were integrated between a lower and upper range. For our tests, we selected ±0.02 Hz from the peak frequency for integration. In both the cases, it is seen that the HF power (i.e., respiration rate, RR) and heart rate (HR) is centered at 0.2 Hz (12 breaths per minute) and 1 Hz (60-61 beats per minute), respectively, which correspond to the fundamental breathing and heart rate measured using conventional sensors (finger pulse oximeter & manual counting of the respiration rate). It is to be noted that, if the reflective plethysmographic signals are not captured accurately, signal reconstruction correction capability may be required. This can be effectuated by detecting peaks and then introducing missing peaks on the detrended signal, band pass filtering, and then performing power spectral density calculations. FIG. 5 shows continuous monitoring of HR, RR and HRV or LF/HF for both (5A) sympathetic and (5B) parasympathetic cases for the same subject for over three minutes. The HRV for the second case, is always less than one which is expected. Evolution of HRV ratio over time contains useful information, especially useful for overnight apnea monitoring and for in-hospital patients who are in a regular hospital bed (inside or outside the ICU). Continuous HRV signals are computed successively with video frames on a batch basis, each new batch uses large part of frames from previous batch and only a few new frames.

Figure 6A:
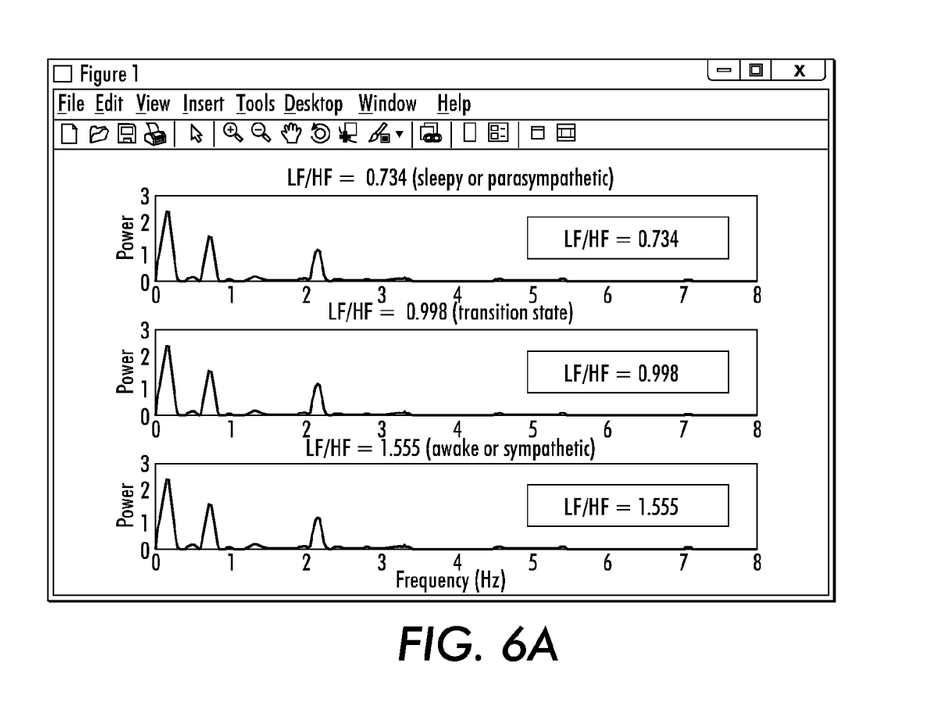
FIG. 6A shows a power spectrum for three successive batches exhibiting HR, RR and HRV assessment of an infant using the teachings hereof.
Figure 6B:
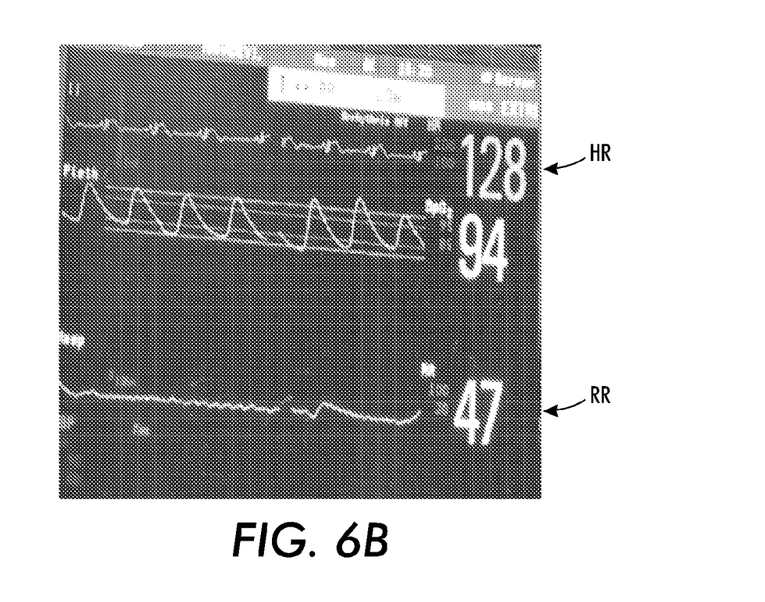
FIG. 6B shows the ground truth recorded from FDA approved Philips health monitoring system, at the time the video of the infant was captured.

FIG. 6A shows a power spectrum for three successive batches exhibiting HR, RR and HRV assessment. FIG. 6B shows the ground truth recorded from FDA approved Philips health monitoring system, at the time the video of the infant was captured. The center frequency of the HR is 2.15 Hz (129 bpm) and RR is 0.75 Hz (45 cpm) which corresponds to the fundamental rates as shown in 6B. The cut-off frequency of 0.04-4 Hz was chosen for bandpass filter. Note how the LF/HF changes from 0.734 (dominant HF) to 0.998 (transition state) to 1.555 (dominant LF) reflecting sympathetic and parasympathetic influences on the infant over time.

Block Diagram of Video Image Processing System

Figure 7:
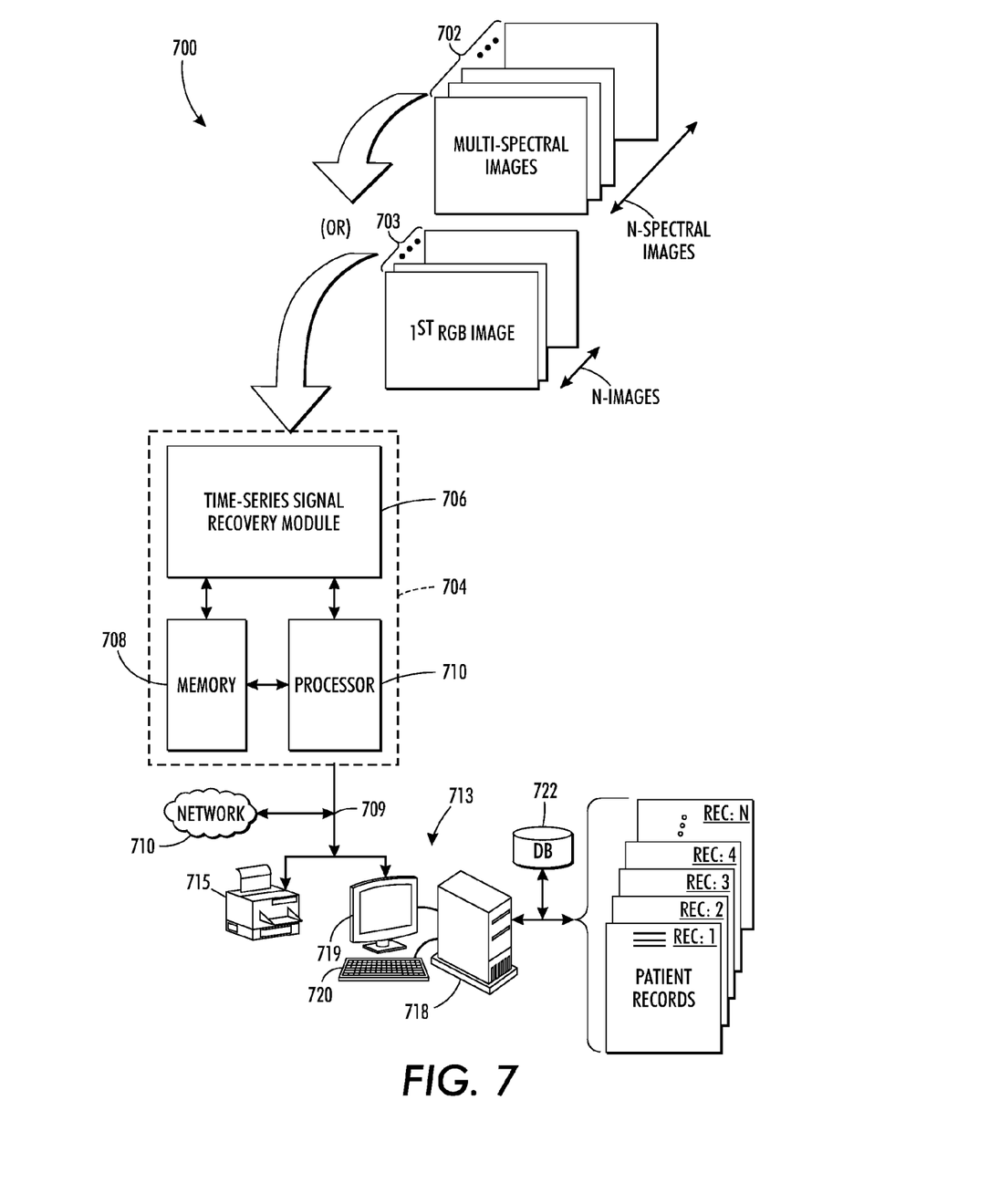
FIG. 7 illustrates a block diagram of one example video image processing system for performing various aspects of the present method as shown and described with respect to the flow diagram of FIG. 3.

Reference is now being made to FIG. 7 which illustrates a block diagram of one example video signal processing system for performing various aspects of the present method as shown and described with respect to the flow diagram of FIG. 3.

The embodiment of FIG. 7 receives a video comprising video images captured of a subject of interest intended to be monitored for cardiac function. The captured video images are either a plurality of IR images 702 captured using a multi-spectral camera or a plurality of RGB images 703. The sequence of images 702 or 703 collectively comprises multi-channel source video data acquired over time. Signal processing system 704 receives the video images into time-series signal recovery module 706 which processes the video images, in accordance with the teachings hereof, to obtain a time-series signal. Memory 708 and CPU 710 facilitate the processing and output the subject's heart rate variability 709. HRV 709 is communicated to workstation 713 and multi-function print system device 715 for further processing and, if desired, rendering. The estimated HRV may further be communicated to remote devices over network 710. Many aspects of network 710 are commonly known and a further discussion as to the construction and/or operation of a specific network configuration has been omitted. Suffice it to say, data is transmitted in packets between networked devices via a plurality of communication devices and links using established protocols. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway.

Computer workstation 713 is shown comprising a computer case 718 housing a motherboard, CPU, memory, interface, storage device, and a communications link such as a network card. The computer workstation is also shown having a display device 719 such as a CRT, LCD, or touchscreen display whereon the HRV is displayed for a technician, nurse, or medical practitioner. Alphanumeric keyboard 720 and a mouse (not shown) effectuate a user input. In the embodiment of FIG. 7, computer system 713 implements database 722 wherein various records are stored, manipulated, and retrieved in response to a query. Such records, in various embodiments, take the form of patient medical history. Although the database is shown as an external device, the database may be internal to computer case 718 mounted on a hard disk housed therein. A record refers to any data structure capable of containing information which can be indexed, stored, searched, and retrieved in response to a query. It should be appreciated that patient medical history information can be stored and/or retrieved to any of the records in database 722. It should also be appreciated that the workstation has an operating system and other specialized software configured to display a variety of numeric values, text, scroll bars, pull-down menus with user selectable options, and the like, for entering, selecting, or modifying information displayed on the display device.

A user of the workstation of FIG. 7 may use the graphical user interface to identify or otherwise select pixels and/or candidate sub-image sections of one or more video frames for processing or re-processing. Menu options selected by a user and any other selections such as regions of exposed skin, video frames, candidate image subsections, proximal and distal regions, and the like, can be communicated to the workstation. Some or all of the received videos may be played by an operator of workstation and viewed on the display, as needed, to facilitate the analysis intended to be performed such that the subject's cardiac function can be monitored. Such facilitation may take the form of the operator selecting one or more frames of the video for analysis and processing. The operator may further direct certain video frames or portions of the received video signals to certain modules and/or processors of the video analysis system of FIG. 7. The generated video analysis result(s) may be reviewed by the user. The operator may modify the results as needed and re-direct the modified results back to the same or different modules for further processing or re-processing. It should be appreciated that the workstation has an operating system and other specialized software configured to display a variety of numeric values, text, scroll bars, pull-down menus with user selectable options, and the like, for entering, selecting, or modifying information displayed on the display device. Upon viewing the computed heart rate variability results, the user may select alternative different regions of exposed skin in the video and provide those to other modules for processing or re-processing. In other embodiments, the generated results are provided directly to a server over network 710 and communicated to a user/operator such as, a physician, nurse, technician, cardiac specialist, to name a few.

Any of the modules and processing units of FIG. 7 are in communication with workstation 713 via pathways (not shown) and may further be in communication with one or more remote devices over network 710. It should be appreciated that some or all of the functionality for any of the modules of system 704 may be performed, in whole or in part, by components internal to workstation 713 or by a special purpose computer system. It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through network 710.

VARIOUS EMBODIMENTS

The teachings hereof can be implemented in hardware or software using any known or later developed systems, structures, devices, and/or software by those skilled in the applicable art without undue experimentation from the functional description provided herein with a general knowledge of the relevant arts. Moreover, the methods hereof can be implemented as a routine embedded on a personal computer or as a resource residing on a server or workstation, such as a routine embedded in a plug-in, a driver, or the like. Furthermore, the teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology described herein. The article of manufacture may be shipped, sold, leased, or otherwise provided separately either alone or as part of an add-on, update, upgrade, or product suite. It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for estimating heart rate variability from a video captured of a subject of interest, the method comprising:
    receiving a video captured of a target area of a region of exposed skin of a subject of interest where a photoplethysmographic (PPG) signal of said subject can be registered, said video comprising video images captured by a video camera;
    selecting a first batch of said video images for processing;
    identifying a first region of interest (ROI) in said selected batch of video images for processing; and
    A) processing pixels in said ROI of said selected batch of said video images to obtain a time-series signal containing a PPG signal captured by said imaging channel of said video camera;
    B) processing said time-series signal to extract said PPG signal;
    C) calculating a power spectral density function on said PPG signal;
    D) using a peak detection algorithm to detect low frequency and high frequency components over a pre-defined frequency range from said power spectral density function;
    E) in response to a low frequency peak or a high frequency peak not being detected in said power spectral density function, performing at least one of:
        (i) identifying a next ROI which is different than said first ROI and repeating again at step (A);
        (ii) selecting a next batch of video images which is at least partially different than said first batch of video images and repeating again at step (A)
        (iii) using signal reconstruction to introduce one or more missing peaks on said PPG signal and then repeating steps (C), (D) and (F); and
    F) determining a ratio of said low and high frequency components over said interval of said selected batch, said ratio comprising said subject's estimated heart rate variability for said interval.

2. The method of claim 1, wherein said target area contains at least a partial view of any of: an anterior thoracic region of said subject, a back region of said subject's dorsal body, a side view of a thoracic region of said subject, an exposed region of said subject's forearm, and exposed region of said subject's palm, a region of said subject's face, a region of said subject's neck, and a region near a finger of said subject.

3. The method of claim 1, wherein video was captured using a video camera comprising any of: an infrared video camera with at least one imaging channel capturing NIR images, a color video camera with at least one imaging channel capturing RGB images, a hybrid infrared and color video camera with imaging channels capturing RGB and NIR images, a multispectral video camera with at least one imaging channel capturing multispectral images, and hyperspectral video camera with at least one imaging channel capturing hyperspectral video images.

4. The method of claim 1, wherein said PPG signal is one of: reflective and transmissive.

5. The method of claim 1, wherein, in advance of extracting said time-series signal, compensating for any of: a motion induced blur, an imaging blur, and slow illuminant variation.

6. The method of claim 1, further comprising communicating said estimated heart rate variability to a display device.

7. The method of claim 1, wherein, in advance of using signal reconstruction to introduce one or more missing peaks, further comprising de-trending said PPG signal followed by band pass filtering.

8. A system for estimating heart rate variability from a video captured of a subject of interest, the system comprising:
   a video camera with at least one imaging channel; and
   a processor in communication with a memory, said processor executing machine readable instructions for performing:
      receiving a video captured of a target area of a region of exposed skin of a subject of interest where a photoplethysmographic (PPG) signal of said subject can be registered, said video comprising video images captured by said video camera;
      selecting a first batch of said video images for processing;
      identifying a first region of interest (ROI) in said selected batch of video images for processing; and
      A) processing pixels in said ROI of said selected batch of said video images to obtain a time-series signal containing a PPG signal captured by said imaging channel of said video camera;
      B) processing said time-series signal to extract said PPG signal;
      C) calculating a power spectral density function on said PPG signal;
      D) using a peak detection algorithm to detect low frequency and high frequency components over a pre-defined frequency range from said power spectral density function;
      E) in response to a low frequency peak or a high frequency peak not being detected in said power spectral density function, performing at least one of:
         (i) identifying a next ROI which is different than said first ROI and repeating again at step (A);
         (ii) selecting a next batch of video images which is at least partially different than said first batch of video images and repeating again at step (A)
         (iii) using signal reconstruction to introduce one or more missing peaks on said PPG signal and then repeating steps (C), (D) and (F); and
      F) determining a ratio of said low and high frequency components over said interval of said selected batch, said ratio comprising said subject's estimated heart rate variability for said interval.

9. The system of claim 8, wherein said target area contains at least a partial view of any of: an anterior thoracic region of said subject, a back region of said subject's dorsal body, a side view of a thoracic region of said subject, an exposed region of said subject's forearm, and exposed region of said subject's palm, a region of said subject's face, a region of said subject's neck, and a region near a finger of said subject.

10. The system of claim 8, wherein said video camera comprises any of: an infrared video camera with at least one imaging channel capturing NIR images, a color video camera with at least one imaging channel capturing RGB images, a hybrid infrared and color video camera with imaging channels capturing RGB and NIR images, a multispectral video camera with at least one imaging channel capturing multispectral images, and hyperspectral video camera with at least one imaging channel capturing hyperspectral video images.

11. The system of claim 8, wherein said PPG signal is one of: reflective and transmissive.

12. The system of claim 8, wherein, in advance of extracting said time-series signal, compensating for any of: a motion induced blur, an imaging blur, and slow illuminant variation.

13. The system of claim 8, further comprising communicating said estimated heart rate variability to a display device.

14. The system of claim 8, wherein, in advance of using signal reconstruction to introduce one or more missing peaks, further comprising de-trending said PPG signal followed by band pass filtering.

15. A computer implemented method for estimating heart rate variability from a video captured of a subject of interest, the method comprising:
   receiving a video captured of a target area of a region of exposed skin of a subject of interest where a photoplethysmographic (PPG) signal of said subject can be registered, said video comprising video images captured by a video camera;
   selecting a first batch of said video images for processing;
   identifying a first region of interest (ROI) in said selected batch of video images for processing; and
   A) processing pixels in said ROI of said selected batch of said video images to obtain a time-series signal containing a PPG signal captured by said imaging channel of said video camera;
   B) processing said time-series signal to extract said PPG signal;
   C) calculating a power spectral density function on said PPG signal;
   D) using a peak detection algorithm to detect low frequency and high frequency components over a pre-defined frequency range from said power spectral density function;
   E) in response to a low frequency peak or a high frequency peak not being detected in said power spectral density function, performing at least one of:
      (i) identifying a next ROI which is different than said first ROI and repeating again at step (A);
      (ii) selecting a next batch of video images which is at least partially different than said first batch of video images and repeating again at step (A)
      (iii) using signal reconstruction to introduce one or more missing peaks on said PPG signal and then repeating steps (C), (D) and (F); and
   F) determining a ratio of said low and high frequency components over said interval of said selected batch, said ratio comprising said subject's estimated heart rate variability for said interval.

16. The computer implemented method of claim 15, wherein said target area contains at least a partial view of any of: an anterior thoracic region of said subject, a back region of said subject's dorsal body, a side view of a thoracic region of said subject, an exposed region of said subject's forearm, and exposed region of said subject's palm, a region of said subject's face, a region of said subject's neck, and a region near a finger of said subject.

17. The computer implemented method of claim 15, wherein video was captured using a video camera comprising any of: an infrared video camera with at least one imaging channel capturing NIR images, a color video camera with at least one imaging channel capturing RGB images, a hybrid infrared and color video camera with imaging channels capturing RGB and NIR images, a multispectral video camera with at least one imaging channel capturing multispectral images, and hyperspectral video camera with at least one imaging channel capturing hyperspectral video images.

18. The computer implemented method of claim 15, wherein said PPG signal is one of: reflective and transmissive.

19. The computer implemented method of claim 15, wherein, in advance of extracting said time-series signal, compensating for any of: a motion induced blur, an imaging blur, and slow illuminant variation.

20. The computer implemented method of claim 15, wherein, in advance of using signal reconstruction to introduce one or more missing peaks, further comprising de-trending said PPG signal followed by band pass filtering.

* * * * *